United States Patent [19]

Lejeune et al.

[11] 3,933,916

[45] Jan. 20, 1976

[54] PURIFICATION OF CYCLOHEXANONE

[75] Inventors: Pierre Lejeune, Wilrijk; Jan Van Esbroeck; Pol Bamelis, both of Kalmthout, all of Belgium

[73] Assignee: Bayer Aktiengesellschaft, Germany

[22] Filed: Sept. 13, 1973

[21] Appl. No.: 397,143

[30]     Foreign Application Priority Data

Sept. 20, 1972　Germany............................ 2246103

[52] U.S. Cl............................ 260/586 R; 260/586 P
[51] Int. Cl.$^2$......................................... C07C 45/24
[58] Field of Search...................... 260/586 R, 586 P

[56]                 References Cited
              UNITED STATES PATENTS 2,387,617   11/1945   Schmidt et al.................. 260/586 R
2,881,215   4/1959    Godt........................... 260/586 R X
3,076,810   2/1963    Duggan et al................... 260/586 R
3,251,753   5/1966    Mueller et al................. 260/586 R X
3,488,391   1/1970    Bende et al.................... 260/586 R

OTHER PUBLICATIONS

Lorette, "J. Org. Chem." Vol. 22, pp. 346–347 (1957).

*Primary Examiner*—Norman Morgenstern
*Attorney, Agent, or Firm*—Connolly and Hutz

[57]            ABSTRACT

Object of the invention is a process for the purification of cyclohexanone which comprises removing impurities from the crude product by adding inorganic or organic acids or ion exchangers. The impurities are degraded and can now be readily separated off by distillation.

5 Claims, No Drawings

PURIFICATION OF CYCLOHEXANONE

This invention relates to a process for the purification of cyclohexanone which can be obtained, for example, by oxidising cyclohexane in air or by hydrogenating phenols.

The cyclohexanone obtained by conventional processes contains impurities which, in the past, it has never been possible to remove completely inspite of all the efforts that have been made. For example, Belgian patent specification No. 714,128 describes one attempt in which the mixture of cyclohexanol and cyclohexanone formed during the oxidation of cyclohexane with air is subjected to gas-phase dehydrogenation in the absence of pressure before further dehydrogenation. In this way, some of the cyclohexanone formed is reduced into cyclohexanol. However, other secondary products are formed at the same time and also have to be removed. Furthermore, this process involves considerable energy and investment costs. It is known from DAS No. 1,188,584 that troublesome impurities can be removed from the crude mixtures containing cyclohexanone by adding alkali hydroxides, alcoholates, phenolates or carbonates to the dehydrogenation mixture, followed by rectification. Unfortunately, the presence of alkali causes uncontrollable aldol condensations which lead to further impurities and, in some cases, to considerable losses of yield. In addition, Belgian patent specification No. 661,116 discloses the use of an aqueous alkaline solution for separating off impurities. An additional disadvantage of this measure is that cyclohexanone is soluble in water to a not inconsiderable extent and, as a result, is lost so far as further working up is concerned. Japanese patent application No. 03184/68 describes a process for purifying cyclohexanone formed by oxidation in air by treating the cyclohexanone solution with basic ion exchangers before distillation. As can be seen from the Example, however, approximately 16% of the crude cyclohexanone used are lost as a resuslt of this measure, presumably because of condensation reactions.

The cyclohexanone solutions accumulating for example after the oxidation of cyclohexanone in air or after the hydrogenation of phenols contains impurities which cannot be separated off at all, or only to an inadequate extent, by conventional methods. Accordingly, there is still a considerable need to develop a purification method which, without excessive outlay on apparatus, enables troublesome impurities to be removed from the cyclohexanone mixture without reducing the yield, especially since these impurities have a considerable influence upon any further reaction to form caprolactam. In addition, these impurities can no longer be separated off after further reaction stages. For these reasons, an extremely pure cyclohexanone is required as starting material for the production of caprolactam because the caprolactam has to satisfy stringent quality requirements.

It has now surprisingly been found that the impurities in the cyclohexanone solution formed for example by the oxidation of cyclohexane in air and by the hydrogenation of phenols can readily be removed to a very considerable extent by adding acids to the solution before it is separated by distillation.

Where the cyclohexanone is produced by the oxidation of cyclohexane in air the acid can be added both before dehydrogenation and also on completion of dehydrogenation.

In the context of the invention, acids include any inorganic and organic compounds which act as acids. Preferred inorganic acids are mineral acids which do not have an oxidising effect under the process conditions, for example, hydrochoric acidic, sulphuric acid and their acidic salts, nitric acidic phosphoric acid and their acidic salts, also mixtures thereof. Suitable organic acids include compounds containing carboxyl and sulphonyl groups, such as aliphatic, cycloaliphatic, aromatic and/or araliphatic mono-, di and/or polycarboxylic and/or sulphonic acids, also mixtures thereof or acid ion exchangers. It is preferred to use acid ion exchangers because they can readily be separated off from the solution. The following compounds are mentioned as examples of organic acids, although the process according to the invention is by no means confined to these compounds: formic acid, acetic acid, propionic acid, caproic acid, oxalic acid, malonic acid, succinic acid, cyclohexyl carboxylic acid, benzoic acid, methyl benzoic acid, phthalic acid, terephthalic acid, maleic acid, citric acid, lactic acid, cyanoacetic acid, nitroacetic acid, methyl sulphonic acid, ethyl sulphonic acid, propyl sulphonic acid, cyclohexyl sulphonic acid, benzene sulphonic acid, paratoluene sulphonic acid, naphthyl sulphonic acids, polyacrylic acid and polymethacrylic acid. Ion exchangers known per se based on synthetic resins containing sulphonyl or carboxyl groups are used as the acid ion exchangers. Particularly suitable synthetic resins include cross-linked polymers and copolymers based on aromatic vinyl compounds such as styrene, vinyl toluene, ethyl styrene, vinyl naphthalene, also copolymers of aromatic monovinyl compounds with other mono-olefinically saturated compounds such as ethylene, propylene or compounds with conjugated carbon-carbon double bonds such as butadiene or chloroprene. Suitable crosslinking agents include aromatic or aliphatic compounds which several vinyl groups, for example, divinyl benzene, substituted divinyl benzenes such as, for example, divinyl toluene, divinyl xylene, divinyl ethyl benzene, and also such compounds as trivinyl benzene, divinyl ethers, divinyl ketones. These copolymers can have both a gel structure and also a sponge structure. The quantity in which the crosslinking agent is used can vary within wide limits. In the case of the gel-structure copolymers, the crosslinking agent is preferably used in quantities of from 0.5 to 20%, based on the monomer total, and, in the case of the sponge-structure copolymers, preferably in quantities of from 2 to 50%, based on the monomer total.

The concentration of the inorganic or organic acid in the cyclohexanone solution can fluctuate within very wide limits. Relatively high concentrations naturally accelerate the purification process. The concentration preferably amounts to from 1 ppm to 1 part by weight and, with particular preference, to from 10 ppm to 0.1 part by weight, based on 100 parts by weight of cyclohexanone solution.

For the same reasons, the ratio of acid ion exchangers to the cyclohexanone solution can vary greatly according to the impurity level.

The acid ion exchangers can be introduced into the cyclohexanone solution and stirred with the solution for a while. However, the cyclohexanone solution can also run through a column filled with acid ion exchangers. The specific load is not critical. The ratio of cyclohexanone solution to ion exchanger is preferably from 100 to 0.1 : 1, and most preferably from 30 to 0.3 : 1.

The ion exchangers used can be regenerated by the usual processes.

It is also necessary in accordance with the invention to dissolve cyclohexanone in an organic solvent. This solvent should not contain any carboxyl groups in the molecule and should be able to be readily separated off from the cyclohexanone by distillation. In general, suitable solvents include aromatic, aliphatic and cycloaliphatic hydrocarbons having from 5 to 15 carbon atoms, for example, pentane, hexane, heptane, octane, nonane, decane, undecane, dodecane, tridecane, tetradecane and pentadecane, as well as their isomers, cyclopentane, cyclohexane, cycloheptane, benzene and benzenes substituted once or several times by alkyl groups, aliphatic and cycloaliphatic alcohols having 1 to 10 carbon atoms for example, methanol, ethanol, propanol, butanol, pentanol, hexanol, heptanol, octanol, nonanol, and decanol and, optionally, their isomers, cyclopentanol and cyclohexanol and their alkyl-substitution products and linear or cyclic ethers having 4 to 15 carbon atoms, for example, dioxane and tetrahydrofuran. Preferred solvents are those products which are present in any event as reactants or as secondary products during or before oxidation or hydrogenation, for example, cyclohexane or cyclohexanol.

The concentration of cyclohexanone in the solvent can amount to from 30 parts by weight, preferably 10 parts by weight, based on 100 parts by weight of the solution.

The temperature at which the process according to the invention is carried out can fluctuate between the melting point of the solution and 150°C, although it is preferably 55°C.

In the process according to the invention, the impurities are degraded and can be readily separated off by distillation.

The purification process according to the invention is illustrated by but by no means limited to the following Examples:

EXAMPLE 1

A solution of cyclohexanone in cyclohexanol, containing approximately 9% of cyclohexanone and 1.47% of impurities, was partially dehydrogenated and then distilled. A certain quantity of first runnings was removed and the cyclohexanone further distilled off until the sump product contained approximately 9% of cyclohexanone. This second fraction is referred to as pure anon. The sump product was concentrated by distillation to 95% and the head product added to the fresh product before dehydrogenation. The cyclohexanone produced in this way still contained 178 ppm of impurities which could be detected by gas chromatography. The separating column was coated with apiezone and the product isothermally eluted at 110°C. A flame ionisation detector was used for the investigations.

When the same solution of cyclohexanone in cyclohexanol was heated with 100 ppm of HCl for 10 minutes to 70°C before dehydrogenation, followed by dehydrogenation and distillation as described above, only 85 ppm of impurities detectable by gas chromatography were obtained in the cyclohexanone.

EXAMPLE 2

A cyclohexanone solution of the kind described in Example 1 was heated for 30 minutes to 150°C with 1 part by weight of caproic acid, followed by dehydrogenation and distillation as described in Example 1. Instead of 178 ppm 94 ppm of impurities detectable by gas chromatography were obtained in the cyclohexanone.

EXAMPLE 3

A cyclohexanone solution of the kind described in Example 1 was heated for 5 minutes to 70°C with 0.1 part by weight of paratoluene sulphonic acid, followed by dehydrogenation and distillation as in Example 1. 85 ppm of of impurities were detected by gas chromatography.

EXAMPLE 4

Before hydrogenation, a 9% solution of cyclohexanone in cyclohexanol was treated for 5 minutes at 55°C with an acid ion exchanger (Lewatit SP 100) and then dehydrogenated and distilled in the same way as in Example 1. Thereafter, only 107 ppm of impurities could be detected by gas chromatography in the cyclohexanone distilled off.

EXAMPLE 5

A 9% solution of cyclohexanol is treated before dehydrogenizing for 5 minutes with an acid ion exchanger which is prepared according to Example 3 of the German patent No. 1,113,570 at 55°C and then dehydrogenized in the same manner as in Example 1 and distilled. Thereafter, only 109 ppm of impurities can be detected gas chromatographically in the distilled cyclohexanone.

EXAMPLE 6

A 9% solution of cyclohexanone in cyclohexanol is treated before dehydrogenizing for 5 minutes with an acid ion exchanger which is prepared according to Example 4 of the German Pat. No. 1,113,570 at 55°C and then dehydrogenized in the same manner as in Example 2 and distilled. Thereafter, only 105 ppm of impurities can be detected gas chromatographically in the distilled cyclohexanone.

We claim:

1. A process for recovering cyclohexanone produced by the air oxidation of cyclohexane or by the hydrogenation of phenol which comprises the steps of dissolving the reaction product of the aforesaid oxidation or hydrogenation in a solvent for cyclohexanone which is readily separated from cyclohexanone by distillation and which is selected from the group consisting of aromatic, aliphatic and cycloaliphatic hydrocarbons of 5 to 15 carbon atoms, alkanols and cycloalkanols of 1 to 10 carbon atoms and their corresponding linear and cyclic ethers having a total of 4 to 15 carbon atoms, treating said solvent solution for up to 30 minutes with an acid at a temperature which is above the solidification point of the solution and up to 150°C. in an amount of from 1 ppm to 1 part by weight of acid per 100 parts by weight of cyclohexanone solution, said acid being selected from the group consisting of mineral acids which do not have an oxidizing effect under said treatment conditions; acidic salts thereof; aliphatic, cycloaliphatic, aromatic and araliphatic carboxylic acids; aliphatic, cycloaliphatic, aromatic and araliphatic sulfonic acids; acid ion exchange resins containing carboxyl groups and acid ion exchange resins containing sulfonyl groups and subsequently distilling said treated solution to recover cyclohexanone.

2. The process of claim 1 wherein said acid is one of said mineral acids or a salt thereof.

3. The process of claim 1 wherein said acid is an acid ion exchange resin containing carboxyl groups or sulfonyl groups and the ratio of cyclohexanone solution to said acid ion exchange resin is from 100 to 0.1:1.

4. The process of claim 1 wherein the concentration of cyclohexanone in said solvent solution is less than 30% by weight.

5. The process of claim 1 wherein said solvent is cyclohexanol, cyclohexane or a mixture thereof.

* * * * *